United States Patent [19]

Trick

[11] Patent Number: 4,550,720
[45] Date of Patent: Nov. 5, 1985

[54] CAPACITANCE DEVICE FOR MEDICAL IMPLANT

[75] Inventor: Robert E. Trick, Racine, Wis.

[73] Assignee: Medical Engineering Corporation, Racine, Wis.

[21] Appl. No.: 551,876

[22] Filed: Nov. 15, 1983

[51] Int. Cl.⁴ .............................................. A61F 5/00
[52] U.S. Cl. ........................................ 128/79; 623/14
[58] Field of Search .......................... 128/79, 344; 3/1

[56] References Cited

U.S. PATENT DOCUMENTS

| | | | |
|---|---|---|---|
| 4,222,377 | 9/1980 | Burton | 128/1 R |
| 4,353,360 | 10/1982 | Finney et al. | 128/79 |
| 4,360,010 | 11/1982 | Finney | 128/79 |
| 4,369,771 | 1/1983 | Trick | 128/79 |
| 4,399,811 | 8/1983 | Finney et al. | 128/79 |
| 4,424,807 | 1/1984 | Evans, Sr. | 128/79 |
| 4,449,520 | 5/1984 | Palomar et al. | 128/79 |

*Primary Examiner*—Paul J. Hirsch
*Attorney, Agent, or Firm*—Quarles & Brady

[57] ABSTRACT

A capacitance device for a medical implant having a hydraulic system including a pressure chamber in which hydraulic pressure must be maintained at a working level comprises an impermeable, elastic bladder which is positioned in the pressure chamber. The bladder is filled with gas so that when fluid is lost from the pressure chamber through leaks within the hydraulic system the bladder will expand to compensate for the fluid loss and prevent severe pressure drops.

7 Claims, 12 Drawing Figures

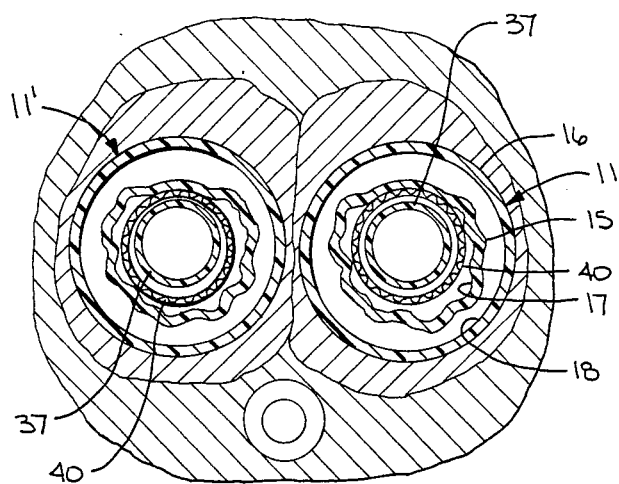
FIG.3
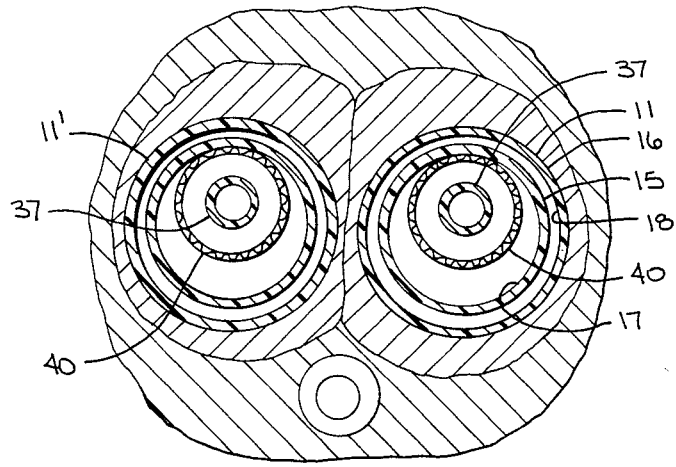
FIG.4
FIG.5
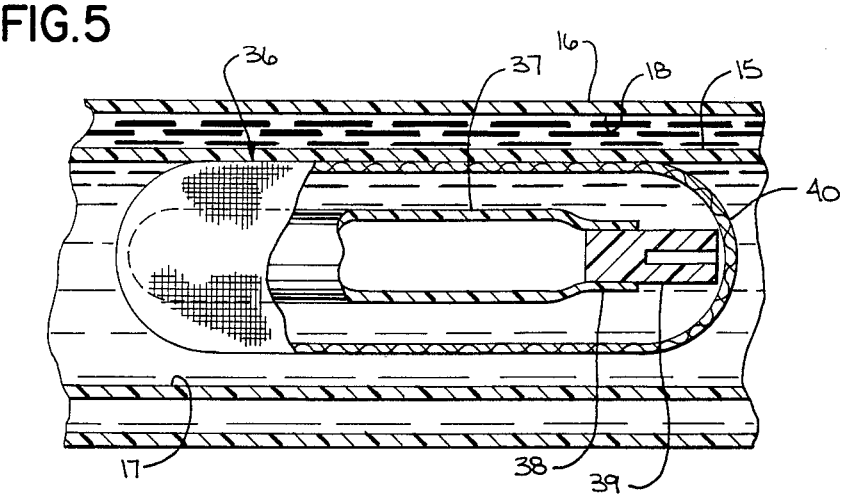

U.S. Patent   Nov. 5, 1985   Sheet 3 of 4   4,550,720
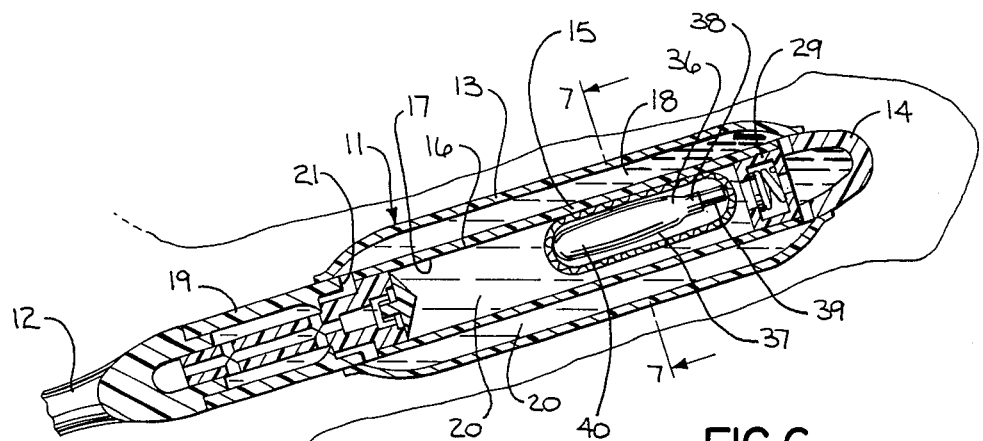
FIG.6
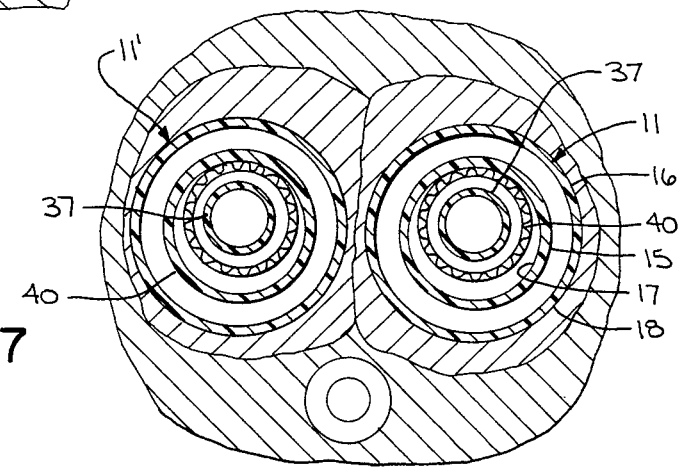
FIG.7
FIG.8 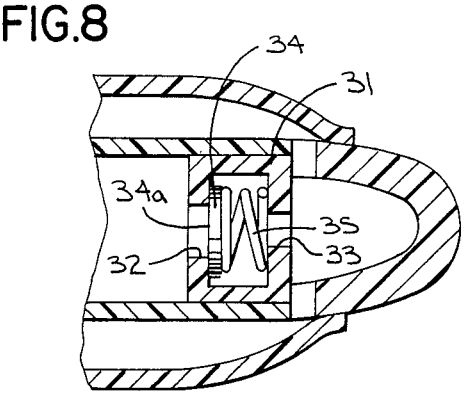   FIG.9 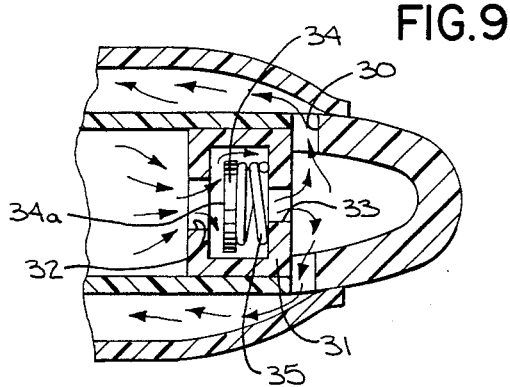

CAPACITANCE DEVICE FOR MEDICAL IMPLANT

TECHNICAL FIELD

The present invention relates to medical implants, such as penile implants and artificial sphincters, which depend on closed hydraulic systems to maintain a working pressure in a pressure chamber for extended periods of times. More particularly, it relates to a novel capacitance device which will compensate for minor leakages in the hydraulic systems of such medical implants, thus preventing pressure drops in the pressure chamber which could necessitate the replacement of the implant.

BACKGROUND OF THE INVENTION

Various medical implants depend upon closed hydraulic systems to maintain a desired working pressure in a pressure chamber for extended periods of time. The artificial sphincter system shown and described in Burton U.S. Pat. No. 4,222,377 is one example of such an implant and the penile implant shown in my earlier U.S. Pat. No. 4,369,771 is another. In the Burton device, the pressure exerted by a pressure chamber in the form of an inflatable cuff is relied upon to keep a body passage closed and in an inflatable penile implant a pressure chamber in the form of a non-distensible cylindrical chamber is pressurized to make it rigid and to make the penis assume an erectible state.

When an implanted medical implant fails to function properly it must be surgically removed and replaced. Therefore, medical implants are carefully made of the finest materials. However, because of the extremely low hydraulic fluid capacitance of such systems and potential leak paths within such systems, minor leakage may occur and any leakage, no matter how slight, can result in a rapid decrease in system pressure causing the implant to fail to function as designed, and requiring its replacement.

In artificial sphincter systems, it is possible, as seen in the forementioned Burton patent, to compensate for minor leaks within the hydraulic system by providing a pressure regulating balloon which is implanted in the abdominal cavity. It would be advantageous to have some smaller effective means of compensating for leaks than the large balloon. The penile implants are intended to be self contained and to be implanted completely within the penis. There is no place in such an implant for a relatively large artificial sphincter type pressure regulating balloon.

There is a need for a small and an effective means of compensating for minor leakages and preventing pressure drops within the hydraulic system of a medical implant which depends upon the maintenance of a pressure in a pressure chamber for extended periods to provide its desired function.

SUMMARY OF THE INVENTION

It is the general object of the present invention to disclose a small and effective capacitance means to compensate for minor internal leaks in the hydraulic systems of medical implants and to prevent pressure drops in the pressure chamber of the implants.

It is a further object to disclose an improved inflatable penile implant which includes a small and effective capacitance means for compensating for minor leaks within the hydraulic system of the penile implant which might otherwise cause pressure drops and require the implant to be replaced.

These and further objects of the invention will be apparent from the description which follows.

The preferred capacitance means of the present invention is a relatively small gas filled impermeable elastic bladder which is located within the pressure chamber of the implant. The gas filled bladder, which is preferably contained within a porous protective bag attached to an inner wall of the pressure chamber, expands in volume to compensate for minor fluid leaks from the pressure chamber and thus functions as a capacitance device or capacitor to prevent severe drops in the pressure within the pressure chamber of the implant.

The capacitance device of the present invention is especially useful in preventing pressure drops in inflatable penile implants used to correct erectile impotence which have low capacitance hydraulic systems and potential leak paths. Such penile implants generally have a nondistensible, cylindrical pressure chamber which is implanted in the pendulous penis. When the pressure chamber is filled with hydraulic fluid under pressure it becomes rigid and causes the penis to assume an erectile state. Any leakage of fluid, even a small amount from the low capacity pressure chamber, can cause a dramatic drop in pressure; as a result, the chamber becomes less rigid and the erectile state is prematurely lost.

The capacitance device of the present invention may also be used in artificial sphincters and other types of medical implants which depend on closed hydraulic systems to maintain pressures in a pressure chamber for an extended period of time. When employed in an artificial sphincter system which depends upon pressure exerted by a pressure chamber in the form of an inflatable member to close a body passage and to prevent body fluids from passing therethrough, the capacitance device of the present invention will preferably be positiond within the inflatable member and attached to an inner wall of the member. When thus positioned, it will be able to expand in volume and compensate for any leakage resulting in volume losses from the pressure chamber. Such volume losses would otherwise cause the member to partially deflate and the body passage to open and allow the escape of body fluid.

BRIEF DESCRIPTION OF DRAWINGS

In the drawings:

FIG. 3 is an enlarged cross sectional view taken along the line 3—3 in FIG. 1;

FIG. 4 is an enlarged cross sectional view taken along the line 4—4 in FIG. 2;

FIG. 5 is an enlarged side view, partly in section, of the capacitance device seen in FIG. 1;

FIG. 6 is a view similar to FIG. 2 but showing the capacitance device expanded in volume to compensate for a loss of volume resulting from internal leakage in the hydraulic system;

FIG. 7 is an enlarged cross sectional view taken along line 7—7 in FIG. 6;

FIG. 8 is an enlarged view, partially in section, of the distal tip portion of the implant of FIG. 1 showing the position of the valve components when the valve is closed; and FIG. 9 is an enlarged view similar to that of FIG. 8 showing the position of the valve components when the valve is open;

BEST MODE OF CARRYING OUT THE INVENTION

Figure 1:
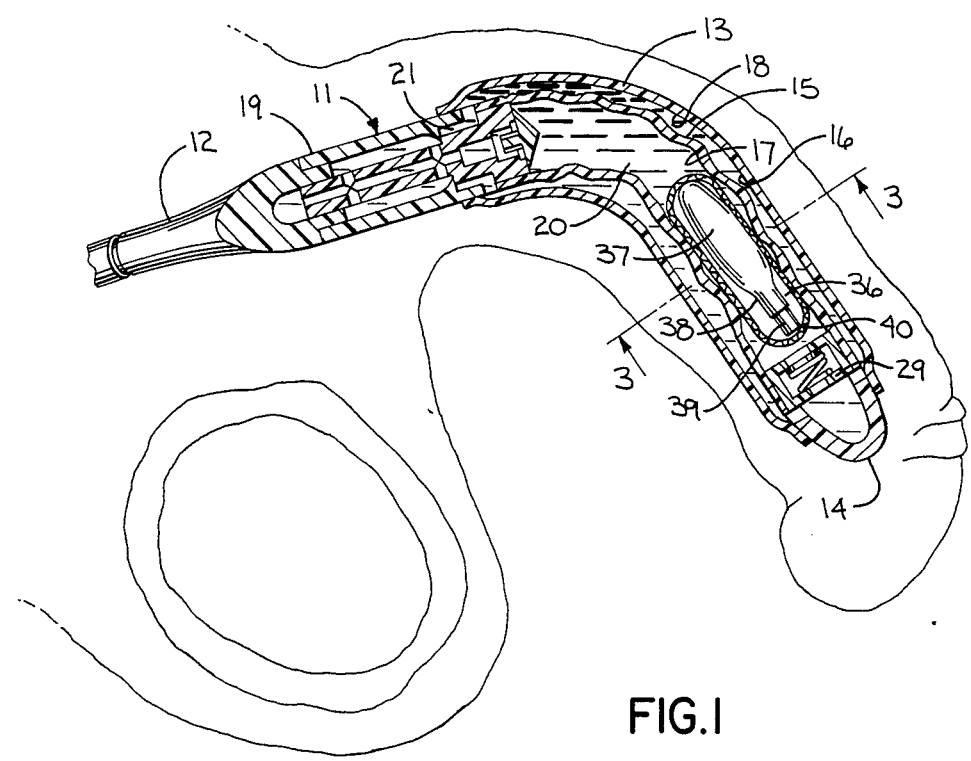
FIG. 1 is a side view, partly in section, of a penile erectile system including a preferred embodiment of the capacitance device of the present invention showing one of the two identical penile implants surgically implanted in a male and in a nonpressurized condition.

The capacitance device of the present invention is especially useful in penile implants which have extremely low capacitance and which have hydraulic systems with potential leak paths. The preferred penile erectile system, which is shown in FIGS. 1-4, comprises a pair of such penile implants 11, 11'. The two implants 11, 11' are identical, therefore, only one will be described in detail.

As seen in FIGS. 1 to 4 of the drawings, the implant 11 has a short, proximal stem 12, an intermediate cylindrical portion 13, and a conical distal tip 14. The stem 12 which is of a relatively stiff material is implanted in the root end of a corpus cavernosum and the cylindrical portion 13 and the tip 14 which are soft and relatively flexible are implanted in the portion of the corpus cavernosum in the pendulus penis. As seen in FIGS. 3, 4 and 7, each of the implants 11, 11' is positioned in a separate corpus cavernosum of the penis.

The intermediate cylindrical portion 13 of the implant 11 includes a pair of concentric cylindrical sleeves 15 and 16 which are attached in a fluid tight manner to the stem 12 and to the tip 14 to form a pair of concentric chambers 17 and 18, respectively. The sleeve 15 which forms the wall of the inner chamber 17 is of an inelastic material such as a silicone coated mesh or woven fabric so that the chamber 17 is non-distensible even when pressurized. The sleeve 15 also cooperates with the sleeve 16 which is spaced outwardly from the sleeve 15 to form the outer chamber 18. The sleeve 16 may be made of a distensible material such as nonreinforced silicone rubber. The necessary fluid tight seals between the sleeves 15 and 16 and the stem 12 and tip 14 may be made with a silicone adhesive or by other suitable means.

As seen in FIGS. 1 and 3, when the implant 11 is in a nonpressurized state both the chambers 17 and 18 are substantially filled with a non-compressible hydraulic fluid 20 which may be a biocompatible fluid such as saline or a free flowing silicone gel. In the non-pressurized state, the soft, flexible, intermediate cylindrical portion 13 of the implant 11 flexes and permits the penis to assume a substantially normal, flaccid position as seen in FIG. 1. However, when the implant 11 is in the pressurized state as seen in FIGS. 2, 4, 6 and 7, the intermediate cylindrical portion 13 is rigid as the result of the non-distensible inner chamber 17 becomes a pressure chamber completely filled with fluid under pressure; the penis then assumes an erectile position.

The pump means, generally referred to as 19, for pressurizing the inner chamber 17 and the pressure control valve 29 for limiting the fluid pressure in the chamber 17 will now be described.

Figure 10:
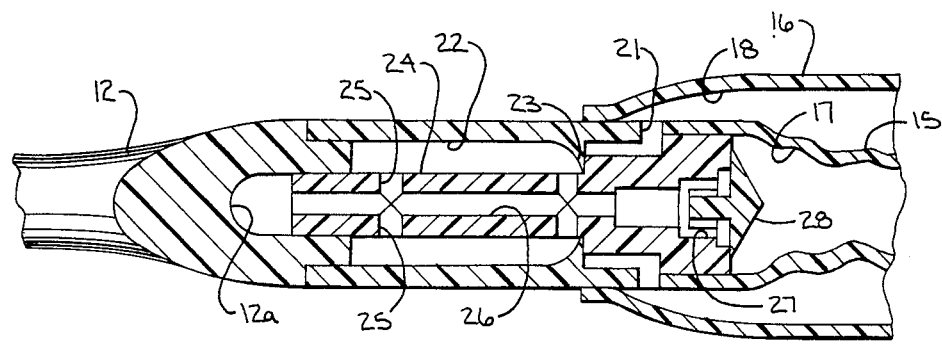
FIG. 10 is an enlarged view, partly in section, of the proximal stem portion of the implant of FIG. 1 showing the position of the pump components when the inner chamber is not pressurized.
Figure 11:
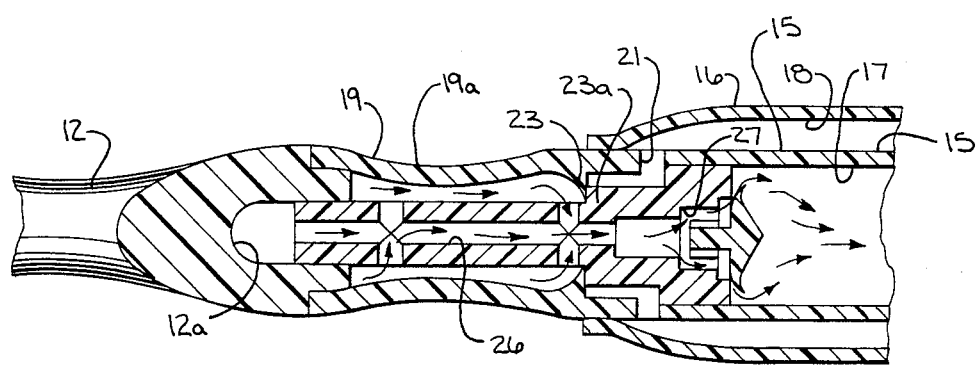
FIG. 11 is an enlarged view similar to that of FIG. 10 showing the position of the pump components when the pump is being used to pressurize the inner chamber.
Figure 12:
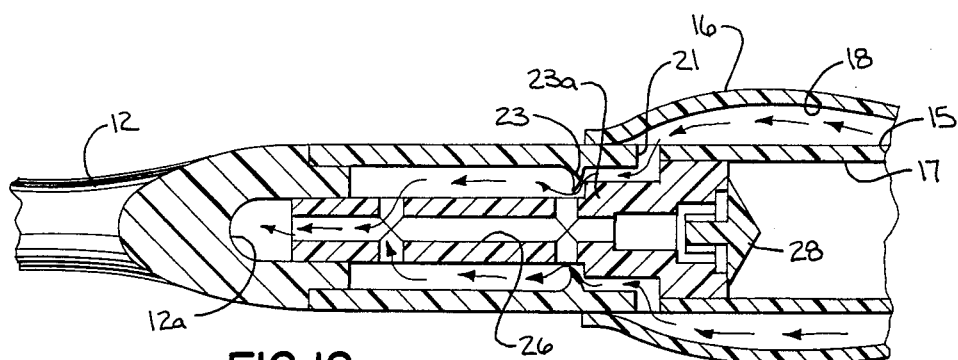
FIG. 12 is an enlarged view similar to that of FIG. 10 showing the pump components when the fluid is flowing from the outer chamber to the pump chamber.

As seen in FIGS. 10, 11 and 12, there is a passage 21 in the proximal portion 12 of the implant 11 which leads from the outer chamber 18 to the pumping chamber 22 of the pump 19. As seen in FIG. 12, the exit of the passage 21 is normally closed by a one way flap valve 23 which opens when the fluid pressure on the valve 23 in the passage 21 exceeds that in the pumping chamber 22 as seen in FIG. 12.

Positioned within the pumping chamber 22 is a support member 24 which has axial passages 25, 25' and a longitudinal passage 26 extending therethrough. The support member 24 extends from and provides communication between the hollow interior 12a of the proximal stem 12, the pumping chamber 22 and the inner chamber 17. The end of the passage 26 opposite the proximal stem 12 has an enlarged exit 27 in which there is positioned a umbrella type flexible check valve 28. The check valve 28 is normally kept seated closing the passage 26 by the fluid pressure in chamber 17. However, when the wall of the pump 19 is squeezed as shown in FIG. 11 the fluid pressure in the pumping chamber 22 and passage 26 exceeds that in chamber 17 and the check valve 28 is opened allowing fluid to flow about the check valve 28 into chamber 17 as indicated by the arrows.

Figure 2:
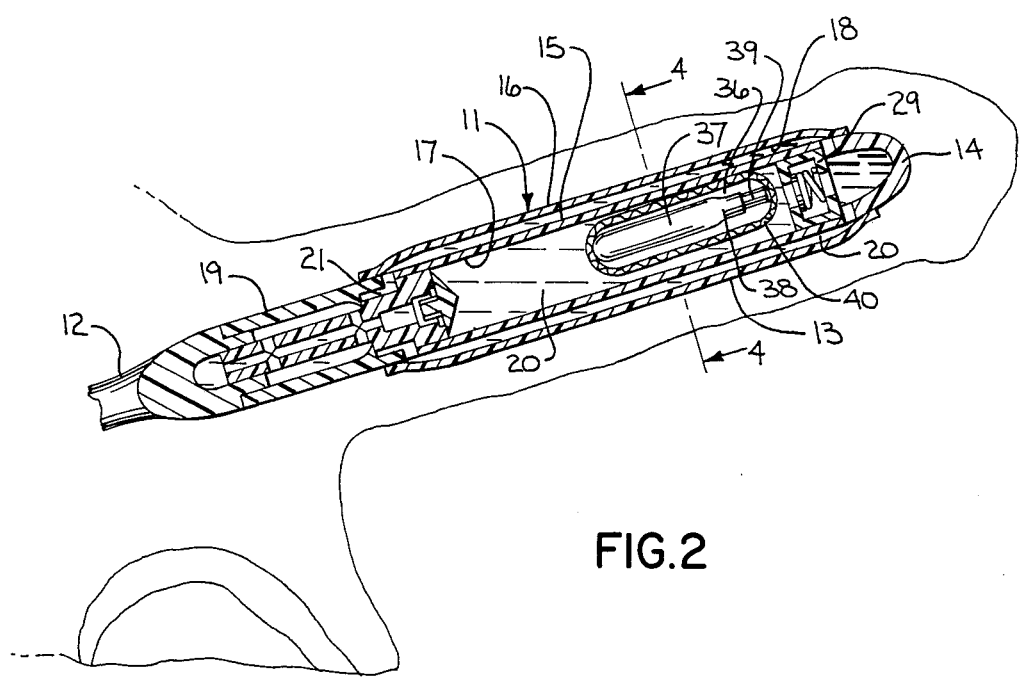
FIG. 2 is a side view similar to FIG. 1, except that the implant is pressurized.

The implant 11 is pressurized by sequentially squeezing the resilient wall 19a of the pump 19 to force the hydraulic fluid 20 under pressure from the pumping chamber 22 into non-distensible inner chamber 17 under pressure and allowing the wall 19a to assume its normal shape. When the pump wall 19a is first squeezed the fluid 20 originally in the pumping chamber 22 is forced through the axial passages 25 and longitudinal passage 26 out the exit 27 forcing the check valve 28 off its seat allowing the fluid 20 to flow about the valve 28 into the pressure chamber 17 (as shown by the arrows in FIG. 11). The increased pressure in the pumping chamber 22 keeps the flap valve 23 seated closing passage 21. Thereafter, when the wall 19a is allowed to assume its normal position, a reduced pressure is formed in the pumping chamber 22 as a result the flap valve 23 is moved off its seat 23a allowing fluid 20 to flow from chamber 18 to enter the pumping chamber 22. When the pressure in pumping chamber 22 equals or exceeds that in chamber 18 the flap valve 23 closes the passage 21. When the pressure chamber 17 is sufficiently pressurized and rigid, the pumping is stopped whereby the exit 27 of the passage 26 is closed by the fluid pressure of the hydraulic fluid 20 in chamber 17 upon the outer surface 28a on the enlarged head of the check valve 28. As a result, the chamber 17 remains filled, pressurized and rigid, as seen in FIG. 2, until the control valve 29 (seen in FIGS. 8 and 9) is opened allowing the fluid 20 to flow via passage 30 back to the chamber 18 whereupon the implant 11 resumes a non-pressurized state.

The preferred pressure control valve 29 which is shown in FIGS. 8 and 9 can be manually opened by squeezing or it will automatically open when the pressure in the pressure chamber 17 exceeds a predetermined level. The valve 29 consists of a valve housing 31 having an inlet 32 and an outlet 33. Located within the housing 31 between the inlet 32 and the outlet 33 is a sealing member 34 and a precalibrated spring 35 which is positioned between the sealing member 34 and the outlet 33. The precalibrated spring 35 normally holds the sealing member 34 seated about the inlet 32 which leads from the inner chamber 17 into the housing 31. When the pressure in the inner chamber 17 which is sensed by the central portion 34a of the sealing member, exceeds the holding force of the precalibrated spring 35 the sealing member 34 is automatically moved from its normal seated position closing the inlet 32 and fluid flows from the inner chamber 17 into the housing 31 and out the outlet 33 and via the passage 30 into the outer chamber 18. Once the pressure sensed by the portion 34a of the sealing member drops below the predetermined level, the calibrated spring 35 reseats the member 34 in its normal position closing the inlet 32.

When it is desired to depressurize the chamber 17 of the implant the valve 29 may be manually opened by squeezing the housing 31 to deform it, thus moving the member 34 away from its normal position closing the inlet 32. Alternatively, the chamber 17 may be depressurized by squeezing the penis and the implant with sufficient force to cause the pressure in chamber 17 to exceed the safe level thereby opening the valve 29 and then continuing the squeezing force until the pressure chamber 17 is sufficiently empty so that the penis will assume a flaccid state. Other types of pressure control valves, of course, may also be used.

The non-distensible inner chamber 17 of the penile implants must when pressurized provide rigidity sufficient to maintain the penis in an erectile position. Therefore, it must be of sufficient volume and size to perform this function either alone or in combination with another implant. In contrast, the outer chamber 18 serves primarily as reservoirs of pressurizing fluid for inner chambers and are sized accordingly. The exact dimensions of the inner and outer chambers are not critical as long as they are adequate to provide their desired function.

The preferred embodiment of the capacitance device of the present invention, designated by the numeral 36, is best seen in FIG. 5. As seen therein it comprises a gas filled, impermeable, elastic bladder 37 having a neck 38 closed by a resealable filler plug 39. The bladder 37 is filled with an inert gas, such as carbon dioxide, preferably at atmospheric pressure or slightly above. The bladder 37 is contained within a non-distensible porous sack 40 which restrains the bladder 37 and protects it from overexpansion and rupture when exposed to sterilization time and temperature.

Referring to FIGS. 1 to 4 and 6 and 7 it can be seen that the sack 40 is fixed to inner wall of the inner pressure chamber 17 to prevent migration. As seen in FIG. 1 the bladder 37 is filled but not excessively stretched when the implant is not pressurized. When the implant is pressurized as seen in FIGS. 2, 4 and 6 and 7 the bladder 37 is smaller in volume because its gas contents are compressed.

In FIGS. 6 and 7 the condition of the implant is depicted when minor leakage through the pump 19, or the control valve 29 has occurred. As seen in therein, the outer chamber 18 contains more fluid than in FIG. 3 and the bladder 37 is larger because it has expanded to compensate for the lower fluid in chamber 17. As a result of the expansion the pressure drop which would have otherwise occurred is minimized.

The bladder 37 is elastic and will expand and contract with its compressible gas contents. A suitable material for the bladder 37 is an elastomer such as bromobutyl rubber, which is highly impermeable under the conditions of use. It has been discovered that if the initial gas pressure in the bladder 37 is slightly above atmospheric pressure the capacitance device will function well in the pressure chamber 17 where pressures can reach up to 900 mm of $H_2O$. The porous sack 40 is preferably made of a nondistensible mesh, such as dacron mesh, and it is large enough to accommodate the expansion of the bladder 37 under normal conditions and to restrain the expansion under the higher temperature conditions of sterilization.

The sleeve 15 which forms the wall of the "non-distensible" pressure chamber 17 must be relatively inelastic and is preferably made of a dacron mesh or fabric covered with silicone material that will not stretch when filled with fluid and pressurized. In contrast, the sleeve 16 may be either distensible or non-distensible. The diameters of the sleeves 15 and 16 can vary but are normally sized so that the implant in the non-pressurized state will fill the corpora cavernosa. It will be appreciated that the term non-distensible or inelastic is intended to cover any material which possesses the desired properties which enable it to provide its described function.

The proximal stem 12 of the implant preferably has a Shore A hardness of about 70, the distal tip 14 a Shore A hardness of about 20, and each of the materials has sufficient tensile strength for its intended use. In the preferred embodiments of the drawings, the tip is tapered and is made of a self-sealing silicone elastomer which allows fluid to be added to or removed from the implant with a fine hollow needle and a syringe.

The term "substantially filled" as used herein to describe the fluid content of a chamber in the penile implant means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

All the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The preferred method of implantation of the erectile system is through an incision made in the penis. After appropriate incision, each corpus cavernosum is dilated distally and proximally to accept the implants. The appropriate anatomical measurements are made to insure that the proximal end of the implant or implants will be positioned at the base of the penis below the pelvic bone. Preferably, the pump is located at the penile base partly under the pubic bone. An implant or implants having an appropriately sized intermediate section and distal tip is inserted into the corpus cavernosum of the penis. The distal tip is positioned in the glans end of the corpus cavernosum. The stem at the proximal end of the implant then is anchored in the root end of the corpus cavernosum.

The identical procedure is performed on the other side of the penis to complete the surgical procedure. The stems of the two implants preferably will diverge laterally to accommodate the anatomy, to provide lateral stability to the penis and to prevent rotation of the implants. The incision is then closed.

It is to be understood that a number of modifications and changes may be made without departing from the spirit and scope of the present invention. For example, although the implants described have solid stems for anchoring the implants, the stems could be hollow and serve as reservoirs. In addition, although implants have been described and illustrated in which there are two concentric chambers it will be appreciated that there could be a single pressure chamber and a reservoir in the stem end as shown in U.S. Pat. No. 4,364,379.

When the medical implant is an artificial sphincter which employs an inflatable cuff or an inflatable pressure chamber of another shape, the capacitance device is preferably located within the pressure chamber and fixed to its inner wall. The capacitance device when thus employed may eliminate the need for the large pressure regulating balloon seen in the Burton patent.

It will be understood that the foregoing description has been for purposes of illustration only and the invention is not to be limited except by the claims which follow.

I claim:

1. In a medical implant having a hydraulic system including a pressure chamber in which hydraulic pressure must be maintained at a working level, the improvement which comprises capacitance means for compensating for hydraulic fluid loss from the pressure chamber and resultant pressure drops, said capacitance means comprising an impermeable bladder located within said pressure chamber, said bladder being elastic and filled with gas under pressure so that it expands to compensate for any minor hydraulic fluid loss from the pressure chamber.

2. The implant of claim 1 in which the bladder contains an inert gas.

3. The implant of claim 1 in which the bladder is positioned within a porous nondistensible protective sack.

4. In a penile implant having a hydraulic system including a nondistensible pressure chamber which is pressurized with hydraulic fluid so as to become rigid and cause the penis to assume an erectile state, the improvement which comprises capacitance means located in the pressure chamber to compensate for hydraulic fluid loss from the pressure chamber as a result of internal hydraulic leaks, said capacitance means comprising an impermeable, elastic bladder which is filled with gas and which will expand to compensate for any minor hydraulic fluid loss from the pressure chamber.

5. The penile implant of claim 4 in which the bladder is filled with an inert gas.

6. The penile implant of claim 4 in which the bladder is positioned within a porous nondistensible protective sack.

7. The implant of claim 6 in which the porous sack is of dacron mesh.

* * * * *